United States Patent [19]

Wickiser

[11] 4,336,264

[45] Jun. 22, 1982

[54] 1-BENZOYL-3-(ISOXAZOLYL OR BENZISOXAZOLYL)-UREAS AND INSECTICIDAL USE THEREOF

[75] Inventor: David I. Wickiser, Indianapolis, Ind.

[73] Assignee: Eli Lilly and Company, Indianapolis, Ind.

[21] Appl. No.: 160,805

[22] Filed: Jun. 19, 1980

[51] Int. Cl.$^3$ .................. A01N 43/76; C07D 263/32; C07D 263/56
[52] U.S. Cl. .................................. 424/272; 548/241; 548/245; 548/246
[58] Field of Search .................. 548/246, 245, 241; 424/272

[56] References Cited

U.S. PATENT DOCUMENTS

| | | | |
|---|---|---|---|
| 3,547,940 | 12/1970 | Brantley | 548/245 |
| 3,748,356 | 7/1973 | Wellinga et al. | 260/553 E |
| 4,014,876 | 3/1977 | Sumatoma et al. | 260/247.2 A |
| 4,062,861 | 12/1977 | Yukinaga | 548/246 |
| 4,083,977 | 4/1978 | Miesel | 424/250 |
| 4,163,784 | 8/1979 | Holland | 424/246 |
| 4,164,581 | 8/1979 | Gibbs | 424/270 |

FOREIGN PATENT DOCUMENTS

| | | | |
|---|---|---|---|
| 2881 | 7/1979 | European Pat. Off. | 548/245 |
| 53-86033 | 7/1978 | Japan . | |
| 54-59272 | 5/1979 | Japan . | |
| 1580876 | 12/1980 | United Kingdom . | |

OTHER PUBLICATIONS

DeMilo, et al., "J. Agri. Food Chem.", vol. 26, No. 1, (1978), pp. 164–166.
DeMilo, et al., "Abstract of Papers", ACS Meeting, 8/28 to 9/2/1977, Chicago.
Wellinga, et al., "J. Agri. Food Chem.", vol. 21, No. 3, (1973), pp. 348–354.
Wellinga, et al., "J. Agri. Food Chem.", vol. 21, No. 6, (1973), pp. 993–998.
Hajjar, et al., "Science", vol. 200, (1978), 1499–1500.

*Primary Examiner*—Anton H. Sutto
*Attorney, Agent, or Firm*—Gerald V. Dahling; Arthur R. Whale

[57] ABSTRACT

The present invention is directed to 1-(benzoyl)-3-(isoxazolyl or benzisoxazolyl)urea or thiourea compounds useful as insecticides.

99 Claims, No Drawings

1-BENZOYL-3-(ISOXAZOLYL OR BENZISOXAZOLYL)-UREAS AND INSECTICIDAL USE THEREOF

SUMMARY OF THE INVENTION

The present invention is directed to novel compounds of the formula

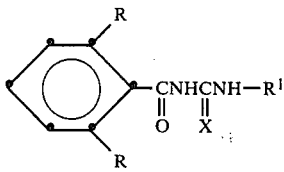

wherein each R is independently selected from the group consisting of:
H,
Br,
Cl,
F,
$CH_3$, or
$OCH_3$,
with the proviso that R cannot simultaneously represent more than one hydrogen atom, and with the further proviso that when one R moiety represents hydrogen the other R moiety cannot simultaneously represent $OCH_3$; X=O or S;
$R^1$ = a 3-isoxazolyl of the formula

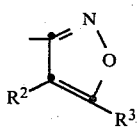

$R^2$ = H,
Br,
Cl,
I,
$C_1$-$C_3$ alkyl, or
CN;
$R^3$ = tert-butyl, phenyl, or meta- or parasubstituted phenyl of which the substituent is chloro, fluoro, $C_2$-$C_4$ alkyl, $C_2$-$C_4$ alkoxy, $O_mC_nF_{2n+1}$, $O_mC_nF_{2n}H$, $-\phi$, or $-O\phi$, m=0-1 and n independently=1-4, with the proviso that when the substituent is fluoro, or chloro, R is not $OCH_3$; or
$R^1$ = a 5-isoxazolyl of the formula

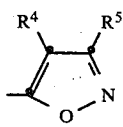

$R^4$ = H,
Br,
Cl,
I,
$C_1$-$C_3$ alkyl, or
CN;
$R^5$ = $CF_3$, tert-butyl, phenyl, or a meta-or-para-substituted phenyl of which the substituent is fluoro, $C_1$-$C_4$ alkyl, $C_1$-$C_4$ alkoxy, $O_mC_nF_{2n+1}$, $O_mC_nF_{2n}H$, $-\phi$, or $-O\phi$,
m=0-1 and n independently=1-4, with the proviso that when the substituent is fluoro, R cannot simultaneously represent more than one chlorine atom; or
$R^1$ = a 3-benzisoxazolyl of the formula

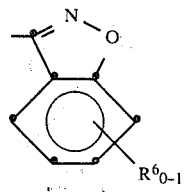

$R^6$ = halo,
$C_1$-$C_4$ alkyl,
$C_1$-$C_4$ alkoxy,
$O_mC_nF_{2n+1}$,
$O_mC_nF_{2n}H$,
$-\phi$, or
$-O\phi$,
m=0-1 and n independently=1-4.

The present invention is also directed to methods employing and compositions comprising the above compounds as insecticides.

DETAILED DESCRIPTION OF THE INVENTION

For the purposes of the present application, the compounds of this invention are named as substituted ureas or substituted thioureas. Therefore the compounds are named, in the case of $R^1$ = a 3-isoxazolyl, as 1-(2-substituted or 2,6-disubstituted benzoyl)-3-(substituted-3-isoxazolyl)ureas or thioureas, or, in the case of $R^1$ = a 5-isoxazolyl, as 1-(2-substituted or 2,6-disubstituted benzoyl)-3-(substituted-5-isoxazolyl)ureas or thioureas, or in the case of $R^1$ = a 3-benzisoxazolyl, as 1-(2-substituted or 2,6-disubstituted benzoyl)-3-(3-benzisoxazolyl or substituted 3-benzisoxazolyl)ureas or thioureas.

The compounds of the present invention are readily prepared by the reaction of a benzoyl isocyanate or benzoyl isothiocyanate of the formula

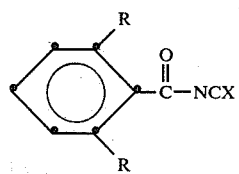

with a 3-aminoisoxazole of the formula

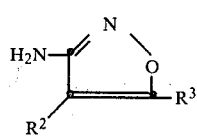

or with a 5-aminoisoxazole of the formula

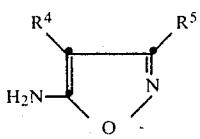

or with a 3-aminobenzisoxazole of the formula

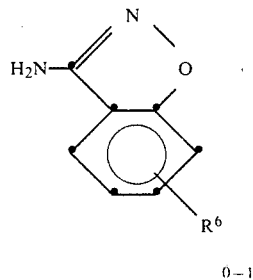

The reaction is a known type of reaction, cf. U.S. Pat. No. 3,748,356. The reaction is conveniently conducted in an organic solvent such as ethyl acetate, $CH_2Cl_2$, toluene, $ClCH_2CH_2Cl$, or DMF, at temperatures ranging from 0° to 60° C. and with equimolar amounts of the reactants.

The benzoyl isocyanates which serve as starting materials are prepared by the reaction of the corresponding benzamide with oxalyl chloride by the method of Speziale et al., *J. Org. Chem.* 27, 3742 (1962). The benzoyl isothiocyanates are also prepared according to conventional procedures by reacting the corresponding benzoyl chlorides with an inorganic thiocyanate such as ammonium thiocyanate, lead thiocyanate, etc.

The 3-aminoisoxazoles to be employed as starting materials are prepared in several synthetic routes, which are outlined below.

(useful only for preparation of $R^2$ = H compounds)

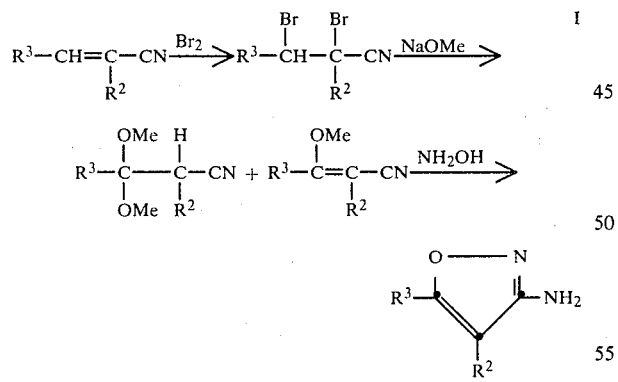

I

This synthetic route is illustrated by Examples 1–3 and 5–7 below.

(useful only for preparation of $R^2$ = H compounds)

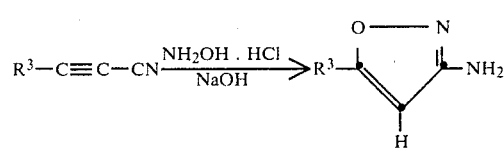

II

This synthetic route is illustrated by Example 9 below.

5 (useful for preparation of $R^2$ = H, $C_1$-$C_3$ alkyl, or CN compounds)

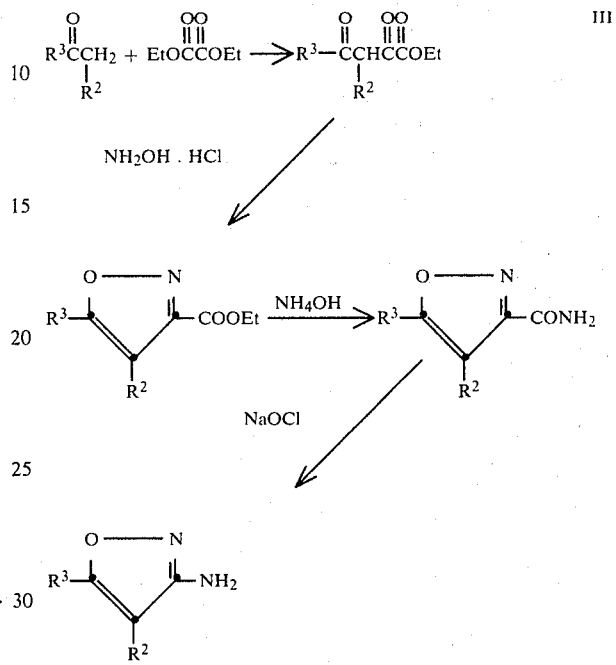

III

This synthetic route is illustrated by Examples 11–14 below.

The 5-aminoisoxazoles to be employed as starting materials are prepared as outlined below.

(useful for preparation of $R^4$ = H, $C_1$-$C_3$ alkyl, or CN compounds)

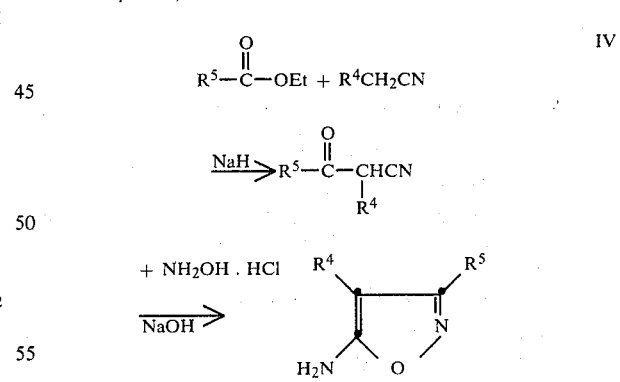

IV

This synthesis route is illustrated by Examples 18–19 below.

The aminoisoxazoles with substituents on the 4-position to be employed as starting materials are also prepared as outlined below.

(useful only for preparation of $R^2$ or $R^4$ = Cl, Br, or I compounds - illustrated here with chlorine for simplicity)

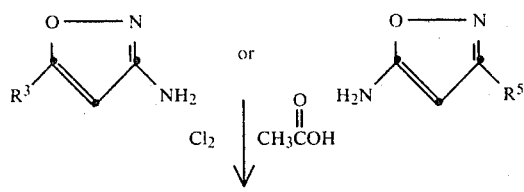

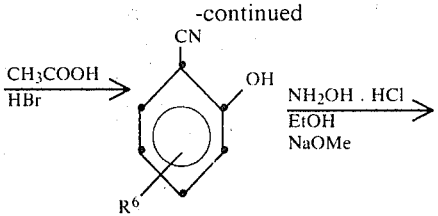

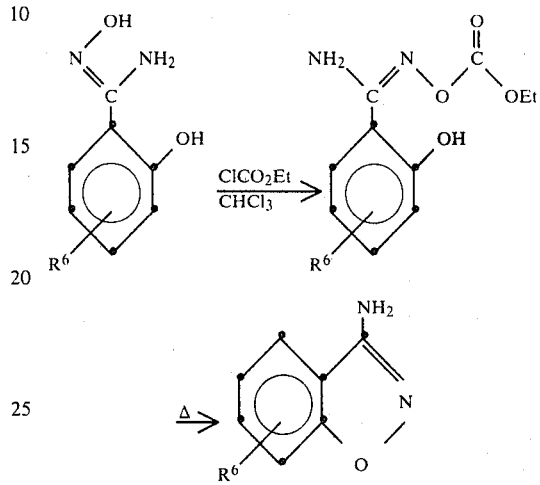

This synthesis route is illustrated by Examples 16 and 22 below.

The benzisoxazoles to be employed as starting materials are prepared according to known procedures as outlined below.

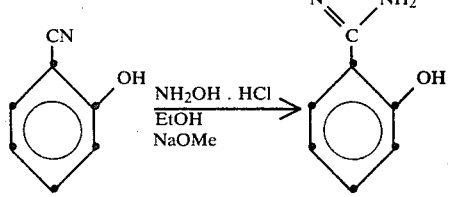

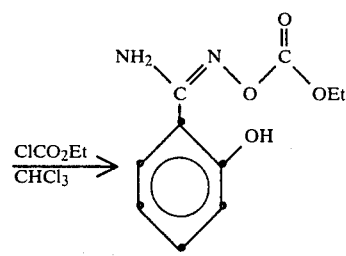

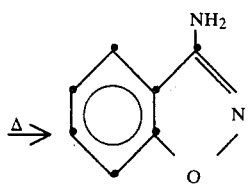

This synthesis route is illustrated by Examples 24–26.

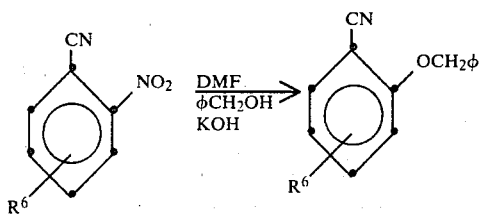

This synthesis route is illustrated by Examples 28–32.

EXAMPLE 1

3-(4-(TRIFLUOROMETHYL)PHENYL)-2,3-DIBROMOPROPIONITRILE 3-(4-(Trifluoromethyl)phenyl)acrylonitrile (1300 grams) was dissolved in chloroform, dried over $Na_2SO_4$, and filtered into a reaction flask. After bromine (1160 grams) was added in a steady stream and over ½ hour period, the reaction mixture was heated to reflux for 32 hours. Next the reaction mixture was stripped which resulted in a brown oil with some solids. The identity of the product was confirmed by NMR, yield 2098 grams.

EXAMPLE 2

MIXTURE OF 3-(4-(TRIFLUOROMETHYL)PHENYL)-3-METHOXYACRYLONITRILE PLUS 3-(4-(TRIFLUOROMETHYL)PHENYL)-3,3-DIMETHOXYPROPIONITRILE 3-(4-(Trifluoromethyl)phenyl)-2,3-dibromopropionitrile (2098 grams) was dissolved in methanol and chilled to 5° C. in an ice-bath. Next, over a 2 hour period, sodium methylate (95%) was added keeping the temperature between 5°–10° C. Following this the reaction mixture was allowed to warm to room temperature, was stirred for 33 hours, and was then stripped to near dryness. Upon the addition of 8 l. ether the mixture was slurried, slowly filtered, and stripped again, resulting in a brown oil. NMR analysis confirmed that the oil was the desired mixture of product.

EXAMPLE 3

5-(4-(TRIFLUOROMETHYL)PHENYL)-3-AMINOISOXAZOLE 3-(4-Trifluoromethyl)phenyl)-3-methoxyacrylonitrile plus 3-(4-(trifluoromethyl)phenyl)-3,3-dimethoxypropionitrile (1330 grams as a mixture) and hydroxylamine.HCl (1180 grams) were dissolved in methanol and chilled to 20° C. in an ice-bath. Next sodium methylate (1890 grams) was added portion-wise over a one and one-half hour period keeping the temperature between 20°–30° C. The reaction mixture was then heated to reflux for about 17 hours and then cooled to 40° C. and filtered. After the filtrate was stripped and poured into ice-water with stirring, a light yellow solid precipitate formed which was filtered and identified by NMR analysis as the desired product, yield 994 grams.

EXAMPLE 4

1-(2,6-DICHLOROBENZOYL)-3-(5-(4-(TRIFLUOROMETHYL)PHENYL)-3-ISOXAZOLYL)UREA 5-(4-(Trifluoromethyl)phenyl)-3-aminoisoxazole (500 grams) in 6 l. 1,2-dichloromethane was reacted in a reaction vessel with 2,6-dichlorobenzoyl isocyanate (567 grams). The isocyanate was added in rapid dropwise fashion over one hour keeping the temperature between 20°–40° C. The reaction mixture was allowed to react at 40° C. for three hours and was then stripped and slurried in 1 l. methanol. A white solid product formed which was filtered, dried in an air dryer, and then identified by NMR analysis as the desired compound, yield, 881 grams, m.p.=227°–230° C.

EXAMPLE 5

3-(4-BIPHENYLYL)-2,3-DIBROMOPROPIONITRILE 3-(4-Biphenylyl)acrylonitrile (10.5 grams) and bromine (9 grams) in 250 ml of chloroform were refluxed overnight (about 18 hours). On cooling, the product precipitated and was separated by filtration, yield 16 grams. NMR confirmed the identity of the product.

EXAMPLE 6

MIXTURE OF 3-(4-BIPHENYLYL)-3-METHOXYACRYLONITRILE PLUS 3-(4-BIPHENYLYL)-3,3-DIMETHOXYPROPIONITRILE 3-(4-Biphenylyl)-2,3-dibromopropionitrile (16 grams) and sodium methoxide (4.7 grams) in 500 ml. of methanol were reacted in an ice bath. A solid precipitated at once and then the reaction mixture was stirred for 2 hours. The final product was determined by NMR to be a mixture of 3-(4-biphenylyl)-3-methoxyacrylonitrile plus 3-(4-biphenylyl)-3,3-dimethoxypropionitrile.

EXAMPLE 7

5-(4-BIPHENYLYL)-3-AMINOISOXAZOLE 3-(4-Biphenylyl)-3-methoxyacrylonitrile plus 3-(4-biphenylyl)-3,3-dimethoxypropionitrile (2.9 grams as a mixture from example 6), hydroxylamine hydrochloride (4.7 grams), and sodium methoxide (11.9 grams) were mixed in 500 ml. of methanol and the reaction mixture refluxed for 48 hours. The methanol was then evaporated, water added, the product separated by filtration, yield 1.2 grams.

EXAMPLE 8

1-(2,6-DICHLOROBENZOYL)-3-(5-(4-BIPHENYLYL)-3-ISOXAZOLYL)UREA 5-(4-Biphenylyl)-3-aminoisoxazole (450 mg.) was mixed with excess 2,6-dichlorobenzoyl isocyanate in 50 ml. of DMF and the reaction mixture stirred overnight (about 18 hours) at room temperature. The reaction mixture was then poured into water and the product separated by filtration and recrystallized from ethanol, m.p. 225°–227° C.

Calc. for $C_{23}H_{15}Cl_2N_3O_3$: C, 61.08; H, 3.34; N, 9.29. Found: C, 61.34; H, 3.28; N, 9.15.

EXAMPLE 9

5-(3-(TRIFLUOROMETHYL)PHENYL)-3-AMINOISOXAZOLE

Hydroxylamine hydrochloride (1.6 grams), and sodium hydroxide (1.6 grams) were dissolved in 32 ml. of a 1:1 mixture of water and methanol at 0°–5° C. 3-(3-(Trifluoromethyl)phenyl)propiolonitrile (2.8 grams) in 10 ml. of methanol was added portionwise, and the reaction mixture was stirred overnight (about 18 hours) at 25° C. Solvent was evaporated; water was added to the residue and the product extracted with ether, washed with water, dried and evaporated, yield 1.4 grams. The identity of the desired product was confirmed by NMR.

EXAMPLE 10

1-(2,6-DICHLOROBENZOYL)-3-(5-(3-(TRIFLUOROMETHYL)PHENYL)-3-ISOXAZOLYL)UREA 5-(3-(Trifluoromethyl)phenyl)-3-aminoisoxazole (300 mg.) and excess 2,6-dichlorobenzoyl isocyanate were mixed in 50 ml. of ethyl acetate under nitrogen, and stirred for several hours at room temperature. The product was separated by filtration, m.p., 233° C. (dec)

Calc. for $C_{18}H_{10}Cl_2F_3N_3O_3$: C, 48.69; H, 2.27; N, 9.46. Found: C, 48.65; H, 2.34; N, 9.74.

EXAMPLE 11

ETHYL 2-(4-tert-BUTYLBENZOYL)PYRUVATE 4-tert-Butylacetophenone (50 grams) and diethyl oxalate (47 grams) were added to a cooled solution (5° C.) of sodium methoxide (18 grams) in methanol. The reaction mixture was stirred for 16 hours with gradual warming to room temperature and then cooled to 0° C. Next 200 ml. of 20% $H_2SO_4$ and 200 ml. of chloroform were added. The layers were separated and the $CHCl_3$ layer washed with 20% $H_2SO_4$, water and brine, then dried over sodium sulfate. Solvent was removed to give a yellow oil. Identity of the product was confirmed by NMR.

EXAMPLE 12

ETHYL 5-(4-tert-BUTYLPHENYL)-3-ISOXAZOLECARBOXYLATE

Ethyl 2-(4-tert-butylbenzoyl)pyruvate (74 grams) was dissolved in 500 ml. of ethanol and hydroxylamine (22.2 grams) and sodium bicarbonate (25.2 grams were added. The reaction mixture was refluxed for 4 hours, and stirred overnight (about 18 hours) at room temperature. The reaction mixture was then poured into 1.2 liter of water. The oil was extracted with ether, washed with water and brine, and dried over magnesium sulfate, yield, 62 grams of crude oil. NMR confirmed the identity of the product.

EXAMPLE 13

5-(4-tert-BUTYLPHENYL)-3-ISOXAZOLECARBOXAMIDE

Ethyl 5-(4-tert-butylphenyl)-3-isoxazolecarboxylate (25 grams) was mixed with 1 liter of concentrated ammonium hydroxide, and the reaction mixture stirred overnight (about 18 hours) at room temperature. The reaction mixture was then poured into 1 liter of water. The product precipitated and was separated by filtration, yield, 34 grams. The structure of the product was confirmed by NMR.

EXAMPLE 14

5-(4-tert-BUTYLPHENYL)-3-AMINOISOXAZOLE 5-(4-tert-Butylphenyl)-3-isoxazolecarboxamide (34 grams), sodium hypochlorite (257.2 grams), and sodium hydroxide (12 grams) were reacted in a bomb, at 0° C. and with agitation, for 1 hour. The reaction mixture was then heated to 150° C., for 5 minutes, cooled to room temperature, and washed with chloroform.

the mixture was then washed further with chloroform and water, and with brine, and then dried over sodium sulfate. Solvent was removed and the product residue recrystallized from diethyl etherethyl acetate, yield, 24 grams, m.p., 180°–182° C. Calc. for $C_{13}H_{16}N_2O$: C, 72.19; H, 7.46; N, 12.96. Found: C, 72.02; H, 7.35; N, 13.16.

EXAMPLE 15

1-(2-CHLOROBENZOYL)-3-(5-(4-tert-BUTYLPHENYL)-3-ISOXAZOLYL)UREA 5-(4-tert-Butylphenyl)-3-aminoisoxazole (1 gram) and 2 chlorobenzoyl isocyanate (1.5 ml.) were mixed in 50 ml. of ethyl acetate. The reaction mixture was stirred for 3 hours at room temperature, solvent removed, and the product separated by filtration, m.p., 213°–214° C.

Calc. for $C_{21}H_{20}ClN_3O_3$: C, 63.40; H, 5.07; N, 10.56. Found: C, 63.19; H, 4.95; N, 10.61.

EXAMPLE 16

4-CHLORO-5-(4-(TRIFLUOROMETHYL)PHENYL)-3-AMINOISOXAZOLE

Chlorine (12.2 grams) was bubbled into 150 ml. acetic acid in a 250 ml. Erlenmeyer flask for 5 minutes. Next 5-(4-(trifluoromethyl)phenyl)-3-aminoisoxazole (25 grams prepared according to the teaching of synthesis route I-III) in 120 ml. acetic acid at 22° C. was added dropwise to this solution over a 25 minute period. The temperature of the reaction mixture rose to 35° C. and was kept between 30°–35° C. during the addition. A precipitate formed. The mixture was then stirred 50 minutes and poured into 1200 ml. ice-water. Next, the precipitate was filtered, washed with water and dried. NMR analysis was used to confirm the identity of the product, yield 20.1 grams, m.p.=115°–118° C.

EXAMPLE 17

1-(2,6-DICHLOROBENZOYL)-3-(4-CHLORO-5-(4-(TRIFLUOROMETHYL)PHENYL)-3-ISOXAZOLYL)UREA

4-Chloro-5-(4-(trifluoromethyl)phenyl)-3-aminoisoxazole was reacted with 2,6-dichlorobenzoyl isocyanate to produce the desired product according to the teaching of Example 8. The identity of the product was confirmed by NMR, m.p.=237°–238° C.

Calculated: C, 45.17; H, 1.90; N, 8.78 Found: C, 45.47; H, 1.82; N, 8.95;

EXAMPLE 18

(4-FLUOROBENZOYL)ACETONITRILE

A 50% solution of NaH (17.6 g., 0.36 mol) was placed in a 500 ml. 3-necked flask under 1 atmosphere of $N_2$ with 200 ml. of dry THF. The reaction mixture was stirred with a magnetic stirring bar, heated to reflux, and, over a 30 minute period, a solution comprised of 52.5 g. (0.32 mol) ethyl 4-fluoobenzoate, 13.5 g. (0.32 mol) acetonitrile, and 40 ml. of THF was added. The reaction mixture was refluxed for an additional two hours during which time hydrogen was evolved. After the evolution ceased, 400 ml. of ether was added and a tan precipitate formed. The precipitate was filtered and then dissolved in 300 ml. of $H_2O$ and acidified with concentrated HCl. The resulting solid product was filtered, dried, and used without further purification.

EXAMPLE 19

3-(4-FLUOROPHENYL)-5-AMINOISOXAZOLE (4-Fluorobenzoyl)acetonitrile (10 g., 0.063 mol) and 200 ml. of ethyl alcohol were placed in a 500 ml. 1-neck flask. To the reaction mixture was added in portionwise fashion a solution comprised of 24 g. of sodium acetate and 18.3 g. of hydroxylamine.HCl in 200 ml. of $H_2O$. After refluxing for three days, the reaction mixture was cooled to room temperature. About half the solvent was removed and then an oily layer formed. The residue was extracted thoroughly in ether and then the combined ether extracts were washed in water, brine, and then dried over $MgSO_4$. When the ether was removed orange crystals formed which were recrystallized from diethyl ether/hexane, m.p., 98°–99° C.

Calculation for $C_{10}H_7FN_2O$: C, 60.67; H, 3.96; N, 15.72. Found: C, 60.96; H, 4.11; N, 15.82.

EXAMPLE 20

1-(2-CHLOROBENZOYL)-3-(3-(4-FLUOROPHENYL)-5-ISOXAZOLYL)UREA 3-(4-Fluorophenyl)-5-aminoisoxazole (250 g.) was combined with 300 g. of 2-chlorobenzoyl isocyanate in 50 ml. of ethyl acetate. The reaction mixture was stirred overnight (about 17 hours) and the resulting solid was filtered, washed with ethanol, ether, and then dried, m.p., 200°–202° C.

Calculation for $C_{17}H_{11}ClFN_3O_3$: C, 56.76; H, 3.08; N, 11.68. Found: C, 57.02; H, 3.32; N, 11.86.

EXAMPLE 21

3-(4-(TRIFLUOROMETHYL)PHENYL)-5-AMINOISOXAZOLE

The desired product was prepared according to the teaching of synthesis route IV. The identity of the product was confirmed by NMR, m.p.=142°–144° C.

EXAMPLE 22

4-CHLORO-3-(4-(TRIFLUOROMETHYL)PHENYL)-5-AMINOISOXAZOLE 3-(4-(Trifluoromethyl)phenyl-5-aminoisoxazole can be reacted accoding to the teaching of Example 16 to produce the desired product.

EXAMPLE 23

1-(2,6-DICHLOROBENZOYL)-3-(4-CHLORO3-(4-(TRIFLUOROMETHYL)PHENYL)-5-ISOXAZOLYL)UREA

4-Chloro-3-(4-trifluoromethyl)phenyl)-5-aminoisoxazole can be reacted with 2,6-dichlorobenzoyl isocyanate to produce the desired product according to the teaching of Example 20.

EXAMPLE 24

2-HYDROXY-BENZAMIDE OXIME

2-Hydroxybenzonitrile (10 grams), hydroxylamine HCl in 150 ml. ethanol, and sodium methoxide (9.0 grams) were refluxed for about 18 hours. The reaction mixture was then filtered and the ethanol evaporated. Next water was added and extracted into ethyl acetate. Drying and evaporation of the solvent left on oily product which solidified upon standing. The identity of the final product was confirmed by NMR and IR analysis.

EXAMPLE 25

2-HYDROXY-O-CARBOETHOXYBENZAMIDE OXIME

2-Hydroxy-benzamide oxime (2.4 grams) in 100 ml. chloroform was added dropwise to ethyl chloroformate (870 mg.) in 5 ml. chloroform. A precipitate formed and the reaction mixture was stirred for 17 hours, filtered, and the chloroform evaporated. The solid material was then dissolved in methanol and, after the addition of water, a precipitate formed which was identified by NMR and IR as the desired product, yield 1.4 grams.

EXAMPLE 26

3-AMINOBENZISOXAZOLE

2-Hydroxy-O-carboethoxybenzamide oxime (1.5 grams) was heated to 135°–140° C. under reduced pressure (5 mm.) and maintained at that temperature until the evolution of gas ceased (about 10 minutes). After cooling, ether was added and then the reaction mixture was filtered and chromatographed (ether-silica gel column chromatography). The material with the highest Rf value was a white solid which was identified by NMR and IR as the desired product, yield 500 mg.

EXAMPLE 27

1-(2,6-DICHLOROBENZOYL)-3-(3-BENZISOXAZOLYL)UREA

3-Aminobenzisoxazole (300 grams) and 2,6-dichlorobenzoyl isocyanate (600 grams) in 50 ml. methylene chloride were stirred at room temperature for one hour. The solvent was then evaporated and the precipitate recrystallized from ethanol. The identity of the product was determined by NMR and IR analysis, yield 500 mg., m.p.=212°–215° C.

Calculated: C, 51.45; H, 2.59; N, 12.00. Found: C, 51.35; H, 2.40; N, 11.84.

EXAMPLE 28

2-(BENZYLOXY)-4-(TRIFLUOROMETHYL)BENZONITRILE

A solution of 2-nitro-4-(trifluoromethyl)benzonitrile (21.5 grams in 350 ml. DMF at 0° C.) and benzyl alcohol (13 grams) was prepared and to this solution potassium hydroxide (10 grams) in 75 ml. water was added dropwise. The reaction mixture was then stirred for about 17 hours and poured into ice water. The resulting precipitate was filtered and identified by NMR as the desired product.

EXAMPLE 29

2-HYDROXY-4-(TRIFLUOROMETHYL)BENZONITRILE 2-(Benzyloxy)-4-(trifluoromethyl)benzonitrile (~20 grams) in 350 ml. acetic acid and 100 ml. 33% HBr was stirred overnight, refluxed for four hours, and then stirred overnight again. Next the reaction mixture was stripped to a small volume and poured into ice water. The crude precipitate which formed was stirred in hexane, filtered, and was identified by NMR as the desired product, yield 9.3 grams.

EXAMPLE 30

2-HYDROXY-4-(TRIFLUOROMETHYL)BENZAMIDE OXIME

The desired compound was prepared according to the teaching of Example 24. The identity of the desired product was confirmed by NMR, yield 6.1 grams from 9.3 g. of starting material.

EXAMPLE 31

2-HYDROXY-4-(TRIFLUOROMETHYL)-O-CARBOETHOXYBENZAMIDE OXIME

The desired compound was prepared according to the teaching of Example 25. The identity of the desired product was confirmed by NMR.

Calculated: C, 45.21; H, 3.79; N, 9.59. Found: C, 44.96; H, 3.76; N, 9.42.

EXAMPLE 32

7-(TRIFLUOROMETHYL)-3-AMINOBENZISOXAZOLE

2-Hydroxy-4-(trifluoromethyl)-O-carboethoxybenzamide oxime (2.1 grams) was heated in a 50 ml. flask under vacuum to a temperature of 190°–195° C. The temperature was maintained at 185°–190° C. until the evolution of gas ceased (about 10 minutes) and then, after cooling, the reaction material was dissolved in ethyl acetate and filtered. TLC (ether) showed no starting material and NMR confirmed the identity of the product.

EXAMPLE 33

1-(2,6-DIFLUOROBENZOYL)-3-(7-(TRIFLUOROMETHYL)-3-BENZISOXAZOLYL)UREA

The desired compound was prepared according to the teaching of Example 27, m.p.=218°–220° C. The identity of the final product was confirmed by NMR.

Calculated: C, 49.88; H, 2.09; N, 10.91. Found: C, 49.61; H, 1.87; N, 11.10.

EXAMPLES 34–64

Other representative compounds of the present invention, synthesized in accordance with the foregoing teaching, include the following.

| Example No. | Compound Name | Melting Point |
| --- | --- | --- |
| 34 | 1-(2-Chlorobenzoyl)-3-(5-(3-(trifluoromethyl)phenyl)-3-isoxazolyl)urea | 193–194° C. |
| 35 | 1-(2,6-Dimethoxybenzoyl)-3-(5-(4-(trifluoromethyl)phenyl)-3-isoxazolyl)urea | 202–204° C. |
| 36 | 1-(2,6-Dichlorobenzoyl)-3-(5-(3-phenoxyphenyl)-3-isoxazolyl)urea | 193–195° C. |
| 37 | 1-(2-Chlorobenzoyl)-3-(4-chloro-5-(4-(trifluoromethyl)phenyl)-3-isoxazolyl)urea | 211–213° C. |
| 38 | 1-(2,6-Difluorobenzoyl)-3-(5-(4-(trifluoromethyl)phenyl)-3-isoxazolyl)urea | 212–214° C. |
| 39 | 1-(2,6-Dichlorobenzoyl)-3-(5-(4-(1,1,2,2-tetrafluoroethoxy)phenyl)-3-isoxazolyl)urea | 189–190° C. |
| 40 | 1-(2,6-Dichlorobenzoyl)-3-(5-(4-tert-butylphenyl)-3-isoxazolyl)urea | 205–207° C. |
| 41 | 1-(2-Methylbenzoyl)-3-(5-(4-trifluoromethyl)phenyl)-3-isoxazolyl)urea | 241–242° C. |
| 42 | 1-(2-Chlorobenzoyl)-3-(5-(4-(trifluoromethyl)phenyl)-3-isoxazolyl)urea | 228–230° C. |
| 43 | 1-(2,6-Dimethoxybenzoyl)-3-(5-tert-butyl-3-isoxazolyl)urea | 226–228° C. |
| 44 | 1-(2,6-Difluorobenzoyl)-3-(4-chloro-5-(4-(trifluoromethyl)phenyl)-3-isoxazolyl)urea | 227–229° C. |
| 45 | 1-(2-Fluorobenzoyl)-3-(5-(4-(trifluoromethyl)phenyl)-3-isoxazolyl)urea | 218–219° C. |
| 46 | 1-(2-Chlorobenzoyl)-3-(4-bromo-5-(4-(trifluoromethyl)phenyl)-3-isoxazolyl)urea | 225–226° C. |
| 47 | 1-(2,6-Dichlorobenzoyl)-3-(5-tert-butyl-3-isoxazolyl)urea | 250–251° C. |
| 48 | 1-(2,6-Dichlorobenzoyl)-3-(4-bromo-5-(4-(trifluoromethyl)phenyl)-3-isoxazolyl)urea | 239–241° C. |
| 49 | 1-(2,6-Difluorobenzoyl)-3-(4-bromo-5-(4-(trifluoromethyl)phenyl)-3-isoxazolyl)urea | 228–229° C. |
| 50 | 1-(2-Chloro-6-methoxybenzoyl)-3-(5-(4-(trifluoromethyl)phenyl)-3-isoxazolyl)urea | 214–215° C. |
| 51 | 1-(2-Chloro-6-fluorobenzoyl)-3-(5-(4-(trifluoromethyl)phenyl)-3-isoxazolyl)urea | 238–240° C. |
| 52 | 1-(2-Chloro-6-fluorobenzoyl)-3-(4-chloro-5-(4-(trifluoromethyl)phenyl)-3-isoxazolyl)urea | 225–226° C. |
| 53 | 1-(2,6-Dichlorobenzoyl)-3-(5-phenyl-3-isoxazolyl)urea | 246–248° C. |
| 54 | 1-(2-chloro-6-fluorobenzoyl)-3-(4-bromo-5-(4-(trifluoromethyl)phenyl)-3-isoxazolyl)urea | 235–236° C. |
| 55 | 1-(2,6-Dichlorobenzoyl)-3-(5-(3-fluorophenyl)-3-isoxazolyl)urea | 207–210° C. |
| 56 | 1-(2,6-Dichlorobenzoyl)-3-(3-(trifluoromethyl)-5-isoxazolyl)urea | 186–189° C. |
| 57 | 1-(2,6-Dichlorobenzoyl)-3-(3-(4-biphenylyl)-5-isoxazolyl)urea | 236–238° C. |
| 58 | 1-(2,6-Dichlorobenzoyl)-3-(3-(4-tolyl-5-isoxazolyl)urea | 223–226° C. |
| 59 | 1-(2,6-Dichlorobenzoyl)-3-(3-(3-(trifluoromethyl)phenyl)-5-isoxazolyl)urea | 235–236° C. |
| 60 | 1-(2,6-Dichlorobenzoyl)-3-(3-tert-butyl-5-isoxazolyl)urea | 199–201° C. |
| 61 | 1-(2,6-Dichlorobenzoyl)-3-(3-phenyl-5-isoxazolyl)urea | 247–249° C. |
| 62 | 1-(2,6-Dichlorobenzoyl)-3-(3-(4-(trifluoromethyl)phenyl-5-isoxazolyl)urea | 245–247° C. |
| 63 | 1-(2,6-Difluorobenzoyl)-3-(3-(4-(trifluoromethyl)phenyl-5-isoxazolyl)urea | 240–243° C. |
| 64 | 1-(2,6-Dimethoxybenzoyl)-3-(3-tert-butyl-5-isoxazolyl)urea | 209–210° C. |

The compounds of the present invention are useful for the control of insects of various orders, including Coleoptera such as Mexican bean beetle, Colorado potato beetle, white grubs; Diptera, such as yellow-fever mosquitoes, house fly; Lepidoptera, such as European corn borer, bollworm, tobacco budworm, *Spodoptera littoralis*, southern armyworn, fall armyworm, sod webworm, tobacco hornworm, loopers, beet armyworm, diamond back moth, imported cabbage worm; Orthoptera, such as German cockroach, American cockroach; and Thysanoptera, such as thrips.

The compounds of the present invention are additionally useful for the control of other insects such as horn fly, common cattle grub, stable fly, face fly, mosquitoes, screwworm, tabanid fly, army cutworm, midges, southwestern corn borer, lesser cornstalk borer, horse bot fly, cabbage maggot, velvet bean caterpillar, pecan nut casebearer, pink bollworm, hickory shuckworm, walnut caterpillar, green cloverworm, alfalfa caterpillar, leaf miner fly, yellowstriped armyworm, rednecked peanutworm, stalk borer, sunflower moth, tomato pin worm, Oriental fruit moth, plum curculio, peachtree borer, melon fly, lesser peachtree borer, grape root borer, black fly, nose bot fly, grape berry moth, sheep ked, leaf rollers, and spruce bud worms.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a compound of the present invention. The locus can be any environment inhabited by insects to be controlled, such as soil, air, water, foods, vegetation, manure, inert objects, stored matter such as grain, and the like. The compounds of the invention will normally be applied by spraying, to the locus in an amount varying from 0.001 to 10 lbs/acre depending on the nature of the locus, the type and severity of the insect infestation, etc. Preferably the compounds are applied in an amount varying from 0.1 to 1 lb/acre.

Preferably the compounds of the present invention are supplied in a formulation, for ease of application. The compounds can be formulated with various adjuvants, including water, organic liquids, surface-active agents, inert solids, and the like. Suitable surface-active agents include anionic agents, such as sodium lauryl sulfate, sodium dodecylbenzenesulfonate, and the like; and nonionic agents, such as polyoxyethylene glycol nonylphenyl ether. Mixtures are often desirably employed. The formulation can take the form of a liquid, dust, granule, aerosol, etc, containing from 0.1 to 90% of a compound of the invention. Specifically the formulation may be an emulsifiable concentrate having 12–50% actives, a wettable powder having up to 80% actives, a granule having up to 10% actives, and a dust having up to 1% actives. The formulation also can be designed to slowly release the active compound or to make the active compound immediately available. Many methods of formulation are known in the art and can be employed to implement the present invention.

The concentration of active agent in the formulation is not critical, inasmuch as an effective concentration will vary with the nature of the locus to be treated, the severity of insect infestation, the susceptibility of the particular insects involved, etc. In general, concentrations ranging from about 0.1 to 1000 ppm give good results. As exemplified by Table 2, below, lesser concentrations of from about 5 to about 100 ppm have given good control of southern armyworm larvae.

While all the compounds of the present invention show considerable efficacy in the control and eradication of undesirable insect pests, certain compounds are more effective than others. Accordingly, preferred compounds of the present invention are those wherein each R, as defined herein, is fluoro and $R^1$ as defined herein, is 3-isoxazolyl with or without a bromo or chloro substituent at the 4-position and with 4-(trifluoromethyl)phenyl at the 5-position. One of the most useful compounds of this preferred group has been shown to be 1-(2,6-difluorobenzoyl)-3-(5-(4-trifluoromethyl)phenyl-3-isoxazolyl)urea. While it is understood that there are many other useful and potentially important embodiments of the present invention, the preferred embodiment is as disclosed herein above.

The insecticidal activity of the present compounds was determined by testing the efficacy of formulations of the compounds against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a plurality of concentrations, from a concentration of about 1000 ppm. to about 1 ppm.

Each compound to be tested was formulated by dissolving the compound in a solvent made up with small amounts of Toximul R and Toximul S, typically 5.9 grams and 4.0 grams, respectively, per liter of 1:1 anhydrous ethanol and acetone. Each of Toximul R and Toximul S is a sulfonate/nonionic blend produced by Stepan Chemical Company, Northfield, Illinois. Water was then added to obtain a solution containing the compound in a concentration of 1000 parts per million. A portion was diluted further with water containing small amounts of Toximul R and Toximul S, to obtain treating solutions of lesser concentrations.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae (*Epilachna varivestis*) and five second- and third-instar southern armyworm larvae (*Spodoptera eridania*) were placed in each of three dishes. The dishes were then placed in a room wherein the temperature and relative humidity were controlled at about 78° F., and about 51 percent, respectively, for a period of four days, at which time the first evaluation of the effects of the test compounds was made. After this evaluation, two fresh leaves from the original treated pots were placed in each dish. The dishes were again maintained in the temperature and humidity controlled room for an additional three days until the final seven-day evaluation was made.

Insecticidal effect was determined by counting the number of living larvae per dish. All the treatments were compared to solvent controls and nontreated controls. The rating code (percent of control) used was as follows:

0 = 0%
1 = 1–50%
2 = 51–99%
3 = 100% control

The results of this test are set forth in Table 1, which follows. In the table column 1 identifies the compounds by the number of the preparative example; column 2 lists the concentration of the test compound in the formulation; and columns 3 through 6 give the Rating Code at days 4 and 7 for the two insects against which the compounds were tested. An N/T entry means 'not tested'.

TABLE 1

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| 4 | 1000 | 0 | 0 | 3 | 3 |
| | 100 | 0 | 0 | 3 | 3 |
| 8 | 1000 | 0 | 0 | 2 | 3 |
| | 100 | 0 | 0 | 1 | 3 |
| 10 | 1000 | 0 | 0 | 1 | 3 |
| | 100 | 0 | 0 | 0 | 3 |
| 15 | 1000 | 3 | 3 | 3 | 3 |
| | 100 | 3 | 3 | 3 | 3 |
| 17 | 1000 | 0 | 2 | 3 | 3 |
| | 100 | 0 | 2 | 3 | 3 |
| 20 | 1000 | 1 | 1 | 1 | 2 |
| | 100 | 0 | 0 | 0 | 0 |
| 27 | 1000 | N/T | N/T | 3 | 3 |
| | 100 | N/T | N/T | 0 | 0 |
| 33 | 1000 | N/T | N/T | 3 | 3 |
| | 100 | N/T | N/T | 1 | 1 |

TABLE 1-continued

| Example No. | Appln. Rate ppm. | Insect Control | | | |
|---|---|---|---|---|---|
| | | Mexican Bean Beetle | | Southern Armyworm | |
| | | 4 days | 7 days | 4 days | 7 days |
| 34 | 1000 | 0 | 1 | 3 | 3 |
| | 100 | 0 | 0 | 2 | 3 |
| 35 | 1000 | 0 | 0 | 3 | 3 |
| | 100 | 0 | 0 | 2 | 3 |
| 36 | 1000 | 0 | 0 | 3 | 3 |
| | 100 | 0 | 0 | 2 | 3 |
| 37 | 1000 | 2 | 3 | 3 | 3 |
| | 100 | 1 | 3 | 3 | 3 |
| 38 | 1000 | 3 | 3 | 3 | 3 |
| | 100 | 3 | 3 | 3 | 3 |
| 39 | 1000 | 1 | 2 | 3 | 3 |
| | 100 | 0 | 1 | 2 | 3 |
| 40 | 1000 | 2 | 3 | 2 | 3 |
| | 100 | 1 | 3 | 1 | 2 |
| 41 | 1000 | 1 | 1 | 3 | 3 |
| | | 0 | 0 | 2 | 3 |
| 42 | 1000 | 1 | 1 | 3 | 3 |
| | 100 | 0 | 0 | 3 | 3 |
| 43 | 1000 | 2 | 3 | 0 | 0 |
| | 100 | 1 | 2 | 0 | 0 |
| 44 | 1000 | 2 | 2 | 3 | 3 |
| | 100 | 1 | 2 | 3 | 3 |
| 45 | 1000 | N/T | N/T | 0 | 2 |
| | 100 | N/T | N/T | 0 | 0 |
| 46 | 1000 | N/T | N/T | 3 | 3 |
| | 100 | N/T | N/T | 3 | 3 |
| 47 | 1000 | 2 | 3 | 3 | 3 |
| | 100 | 0 | 2 | 2 | 2 |
| 48 | 1000 | N/T | N/T | 3 | 3 |
| | 100 | N/T | N/T | 3 | 3 |
| 49 | 1000 | N/T | N/T | 3 | 3 |
| | 100 | N/T | N/T | 3 | 3 |
| 50 | 1000 | N/T | N/T | 3 | 3 |
| | 100 | N/T | N/T | 3 | 3 |
| 51 | 1000 | N/T | N/T | 3 | 3 |
| | 100 | N/T | N/T | 3 | 3 |
| 52 | 1000 | N/T | N/T | 3 | 3 |
| | 100 | N/T | N/T | 3 | 3 |
| 53 | 1000 | 0 | 0 | 2 | 3 |
| | 100 | 0 | 0 | 1 | 1 |
| 54 | 1000 | N/T | N/T | 3 | 3 |
| | 100 | N/T | N/T | 3 | 3 |
| 55 | 1000 | 0 | 0 | 2 | 3 |
| | 100 | 0 | 0 | 1 | 2 |
| 56 | 1000 | 0 | 0 | 3 | 3 |
| | 100 | 0 | 0 | 1 | 2 |
| 57 | 1000 | 0 | 0 | 0 | 1 |
| | 100 | N/T | N/T | N/T | N/T |
| 58 | 1000 | 2 | 2 | 0 | 0 |
| | 100 | N/T | N/T | N/T | N/T |
| 59 | 1000 | 2 | 2 | 2 | 3 |
| | 100 | N/T | N/T | N/T | N/T |
| 60 | 1000 | 0 | 1 | 3 | 3 |
| | 100 | 0 | 1 | 2 | 2 |
| 61 | 1000 | 1 | 1 | 1 | 1 |
| | 100 | 0 | 1 | 0 | 0 |
| 62 | 1000 | 0 | 2 | 2 | 3 |
| | 100 | 0 | 0 | 0 | 0 |
| 63 | 1000 | N/T | N/T | 3 | 3 |
| | 100 | N/T | N/T | 2 | 2 |
| 64 | 1000 | 3 | 3 | 0 | 0 |
| | 100 | 2 | 3 | 0 | 0 |

The compounds of the present invention were also tested in the same procedure described above but at lower concentrations. In these tests, percent control was determined by counting the number of living larvae per dish and using Abbott's formula [W. W. Abbott, "A Method of Computing the Effectiveness of an Insecticide", *J. Econ. Entomol.* 18, 265–267 (1925)]:

Percent Control =

$$\frac{\text{No. of survivors in control} - \text{No. of survivors in treatment} \times 100}{\text{No. survivors in control}}$$

The results are set forth in Table 2, which follows.

TABLE 2

| Example No. | Appln. Rate ppm. | Insect Control (%) | | | |
|---|---|---|---|---|---|
| | | Mexican Bean Beetle | | Southern Armyworm | |
| | | 4 days | 7 days | 4 days | 7 days |
| 4 | 100 | N/T | N/T | 100 | 100 |
| | 50 | " | " | 100 | 100 |
| | 25 | " | " | 86 | 100 |
| | 10 | " | " | 0 | 93 |
| 4 | 10. | N/T | N/T | 67 | 100 |
| | 5. | " | " | 13 | 100 |
| | 2.5 | " | " | 0 | 79 |
| | 1.0 | " | " | 0 | 43 |
| 8 | 100 | N/T | N/T | 87 | 100 |
| | 50 | " | " | 53 | 100 |
| | 25 | " | " | 7 | 40 |
| | 10 | " | " | 13 | 13 |
| 10 | 100 | N/T | N/T | 100 | 100 |
| | 50 | " | " | 93 | 100 |
| | 25 | " | " | 33 | 100 |
| | 10 | " | " | 0 | 36 |
| 15 | 100 | 100 | 100 | 47 | 67 |
| | 50 | 72 | 100 | 0 | 0 |
| | 25 | 72 | 100 | 0 | 20 |
| | 10 | 0 | 53 | 0 | 0 |
| 17 | 100 | N/T | N/T | 100 | 100 |
| | 50 | " | " | 100 | 100 |
| | 25 | " | " | 100 | 100 |
| | 10 | " | " | 40 | 67 |
| 34 | 100 | 100 | 100 | N/T | N/T |
| | 50 | 100 | 100 | " | " |
| | 25 | 100 | 100 | " | " |
| | 10 | 73 | 73 | " | " |
| 34 | 10. | N/T | N/T | 40 | 100 |
| | 5. | " | " | 27 | 53 |
| | 2.5 | " | " | 13 | 20 |
| | 1.0 | " | " | 0 | 0 |
| 35 | 100 | N/T | N/T | 93 | 100 |
| | 50 | " | " | 86 | 100 |
| | 25 | " | " | 53 | 100 |
| | 10 | " | " | 13 | 13 |
| 36 | 100 | N/T | N/T | 100 | 100 |
| | 50 | " | " | 100 | 100 |
| | 25 | " | " | 100 | 100 |
| | 10 | " | " | 20 | 67 |
| 37 | 100 | 100 | 100 | 100 | 100 |
| | 50 | 86 | 93 | 100 | 100 |
| | 25 | 86 | 93 | 100 | 100 |
| | 10 | 73 | 80 | 100 | 100 |
| 37 | 10 | 0 | 60 | 100 | 100 |
| | 5 | 27 | 60 | 80 | 100 |
| | 2.5 | 33 | 0 | 80 | 93 |
| | 1 | 0 | 0 | 27 | 33 |
| 38 | 100 | 40 | 60 | 100 | 100 |
| | 50 | 27 | 47 | 100 | 100 |
| | 25 | 20 | 40 | 100 | 100 |
| | 10 | 20 | 40 | 100 | 100 |
| 38 | 10 | 0 | 0 | 100 | 100 |
| | 5 | 0 | 0 | 100 | 100 |
| | 2.5 | 0 | 0 | 100 | 100 |
| | 1 | 0 | 0 | 87 | 100 |
| 38 | 1.0 | N/T | N/T | 100 | 100 |
| | 0.5 | " | " | 53 | 87 |
| | 0.25 | " | " | 0 | 7 |
| | 0.125 | " | " | 0 | 20 |
| 39 | 100 | N/T | N/T | 100 | 100 |
| | 50 | " | " | 100 | 100 |
| | 25 | " | " | 93 | 93 |
| | 10 | " | " | 93 | 93 |
| 40 | 100 | N/T | N/T | 47 | 87 |
| | 50 | " | " | 27 | 40 |
| | 25 | " | " | 40 | 60 |
| | 10 | " | " | 27 | 27 |
| 41 | 100 | 100 | 100 | N/T | N/T |
| | 50 | 100 | 100 | " | " |
| | 25 | 87 | 100 | " | " |

TABLE 2-continued

| Example No. | Appln. Rate ppm. | Insect Control (%) | | | |
|---|---|---|---|---|---|
| | | Mexican Bean Beetle | | Southern Armyworm | |
| | | 4 days | 7 days | 4 days | 7 days |
| | 10 | 33 | 100 | " | " |
| 41 | 10. | N/T | N/T | 67 | 100 |
| | 5. | " | " | 53 | 93 |
| | 2.5 | " | " | 27 | 73 |
| | 1.0 | " | " | 0 | 7 |
| 42 | 100 | 100 | 100 | N/T | N/T |
| | 50 | 100 | 100 | " | " |
| | 25 | 100 | 100 | " | " |
| | 10 | 100 | 100 | " | " |
| 42 | 10. | N/T | N/T | 87 | 100 |
| | 5. | " | " | 87 | 93 |
| | 2.5 | " | " | 27 | 73 |
| | 1.0 | " | " | 0 | 7 |
| 44 | 100 | N/T | N/T | 100 | 100 |
| | 50 | " | " | 100 | 100 |
| | 25 | " | " | 100 | 100 |
| | 10 | " | " | 100 | 100 |
| 44 | 10 | N/T | N/T | 100 | 100 |
| | 5. | " | " | 100 | 100 |
| | 2.5 | " | " | 100 | 100 |
| | 1 | " | " | 0 | 0 |
| 47 | 100 | N/T | N/T | 27 | 60 |
| | 50 | " | " | 7 | 40 |
| | 25 | " | " | 0 | 27 |
| | 10 | " | " | 0 | 0 |
| 50 | 10 | N/T | N/T | 0 | 0 |
| | 5 | " | " | 0 | 0 |
| | 2.5 | " | " | 0 | 0 |
| | 1 | " | " | 53 | 100 |
| 51 | 10 | N/T | N/T | 100 | N/T |
| | 5 | " | " | 100 | " |
| | 2.5 | " | " | 100 | " |
| | 1. | " | " | 100 | 60 |
| 52 | 10. | N/T | N/T | 100 | N/T |
| | 5. | " | " | 100 | " |
| | 2.5 | " | " | 100 | 100 |
| | 1 | " | " | 0 | 80 |
| 59 | 100 | N/T | N/T | 68 | 40 |
| | 50 | " | " | N/T | N/T |
| | 25 | " | " | " | " |
| | 10 | " | " | " | " |

I claim:

1. Compound of the formula

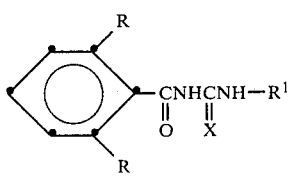

wherein each R is independently selected from the group consisting of:
H,
Br,
Cl,
F,
CH$_3$, or
OCH$_3$,
with the proviso that R cannot simultaneously represent more than one hydrogen atom, and with the further proviso that when one R moiety represents hydrogen the other R moiety cannot simultaneously represent OCH$_3$; X = O or S;
R$^1$ = a 3-isoxazolyl of the formula

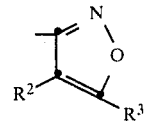

R$^2$ = H,
Br,
Cl,
I,
C$_1$-C$_3$ alkyl, or
CN;
R$^3$ = tert-butyl, phenyl, or meta- or para-substituted phenyl of which the substituent is chloro, fluoro, C$_2$-C$_4$ alkyl, C$_2$-C$_4$ alkoxy, O$_m$C$_n$F$_{2n+1}$, O$_m$C$_n$F$_{2n}$H, $-\phi$, or $-O\phi$, m = 0-1 and n independently = 1-4, with the proviso that when the substituent is fluoro, or chloro, R is not OCH$_3$; or
R$^1$ = a 5-isoxazolyl of the formula

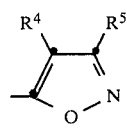

R$^4$ = H,
Br,
Cl,
I,
C$_1$-C$_3$ alkyl, or
CN; and
R$^5$ = CF$_3$, tert-butyl, phenyl, or a meta-or-para-substituted phenyl of which the substituent is fluoro, C$_1$-C$_4$ alkyl, C$_1$-C$_4$ alkoxy, O$_m$C$_n$F$_{2n+1}$, O$_m$C$_n$F$_{2n}$H, $-\phi$, or $-O\phi$,
m = 0-1 and n independently = 1-4, with the proviso that when the substituent is fluoro, R cannot simultaneously represent more than one chlorine atom; or
R$^1$ = a 3-benzisoxazolyl of the formula

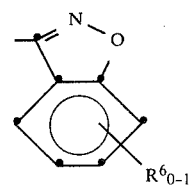

R$^6$ = halo,
C$_1$-C$_4$ alkyl,
C$_1$-C$_4$ alkoxy,
O$_m$C$_n$F$_{2n+1}$,
O$_m$C$_n$F$_{2n}$H,
$-\phi$, or
$-O\phi$,
m = 0-1 and n independently = 1-4.

2. The compound of claim 1 wherein R$^1$ is 3-isoxazolyl as recited in claim 1.

3. The compound of claim 2 wherein R$^3$ is 4-(trifluoromethyl)phenyl.

4. The compound of claim 3 which is 1-(2,6-dichlorobenzoyl)-3-(5-(4-(trifluoromethyl)phenyl)-3-isoxazolyl)urea.

5. The compound of claim 3 which is 1-(2,6-difluorobenzoyl)-3-(5-(4-(trifluoromethyl)phenyl)-3-isoxazolyl)urea.

6. The compound of claim 3 which is 1-(2,6-dimethoxybenzoyl)-3-(5-(4-(trifluoromethyl)phenyl)-3-isoxazolyl)urea.

7. The compound of claim 3 which is 1-(2-methylbenzoyl)-3-(5-(4-(trifluoromethyl)phenyl)-3-isoxazolyl)urea.

8. The compound of claim 3 which is 1-(2-chlorobenzoyl)-3-(5-(4-(trifluoromethyl)phenyl)-3-isoxazolyl)urea.

9. The compound of claim 3 which is 1-(2-chloro-6-fluorobenzoyl)-3-(5-(4-(trifluoromethyl)phenyl)-3-isoxazolyl)urea.

10. The compound of claim 3 wherein $R^2$ is chloro or bromo.

11. The compound of claim 10 which is 1-(2,6-dichlorobenzoyl)-3-(4-chloro-5-(4-(trifluoromethyl)phenyl)-3-isoxazolyl)urea.

12. The compound of claim 10 which is 1-(2-chlorobenzoyl)-3-(4-chloro-5-(4-(trifluoromethyl)phenyl)-3-isoxazolyl)urea.

13. The compound of claim 10 which is 1-(2,6-difluorobenzoyl)-3-(4-chloro-5-(4-(trifluoromethyl)phenyl)-3-isoxazolyl)urea.

14. The compound of claim 10 which is 1-(2-chloro-6-fluorobenzoyl)-3-(4-chloro-5-(4-trifluoromethyl)phenyl)-3-isoxazolyl)urea.

15. The compound of claim 10 which is 1-(2-chlorobenzoyl)-3-(4-bromo-5-(4-(trifluoromethyl)phenyl)-3-isoxazolyl)urea.

16. The compound of claim 10 which is 1-(2,6-dichlorobenzoyl)-3-(4-bromo-5-(4-(trifluoromethyl)phenyl)-3-isoxazolyl)urea.

17. The compound of claim 10 which is 1-(2,6-difluorobenzoyl)-3-(4-bromo-5-(4-(trifluoromethyl)phenyl)-3-isoxazolyl)urea.

18. The compound of claim 10 which is 1-(2-chloro-6-fluorobenzoyl)-3-(4-bromo-5-(4-(trifluoromethyl)phenyl)-3-isoxazolyl)urea.

19. The compound of claim 2 wherein $R^3$ is 4-(1,1,2,2-tetrafluoroethoxy)phenyl.

20. The compound of claim 19 which is 1-(2,6-dichlorobenzoyl)-3-(5-(4-(1,1,2,2-tetrafluoroethoxy)phenyl)-3-isoxazolyl)urea.

21. The compound of claim 2 wherein $R^3$ is 3-(trifluoromethyl)phenyl.

22. The compound of claim 21 which is 1-(2-chlorobenzoyl)-3-(5-(3-(trifluoromethyl)phenyl-3-isoxazolyl)urea.

23. The compound of claim 1 wherein $R^1$ is 5-isoxazolyl as recited in claim 1.

24. The compound of claim 23 wherein $R^5$ is 4-(trifluoromethyl)phenyl.

25. The compound of claim 24 which is 1-(2,6-dichlorobenzoyl)-3-(3-(4-(trifluoromethyl)phenyl)-5-isoxazolyl)urea.

26. The compound of claim 23 wherein $R^5$ is 3-(trifluoromethyl)phenyl.

27. The compound of claim 26 which is 1-(2,6-dichlorobenzoyl)-3-(3-(3-(trifluoromethyl)phenyl)-5-isoxazolyl)urea.

28. The compound of claim 23 wherein $R^5$ is trifluoromethyl.

29. The compound of claim 28 which is 1-(2,6-dichlorobenzoyl)-3-(3-trifluoromethyl)-5-isoxazolyl)urea.

30. The compound of claim 1 wherein $R^1$ is a 3-benzisoxazolyl as recited in claim 1.

31. The compound of claim 30 which is 1-(2,6-dichlorobenzoyl)-3-(3-benzisoxazolyl)urea.

32. The compound of claim 30 wherein $R^6$ is trifluoromethyl.

33. The compound of claim 32 which is 1-(2,6-difluorobenzoyl)-3-(6-trifluoromethyl)-3-benzisoxazolyl)urea.

34. Method of suppressing insects of an order selected from the group consisting of Coleoptera, Diptera, Lepidoptera, and Orthoptera, which comprises applying to the locus of the insects an effective amount of an active agent which is a compound of claim 1.

35. The method of claim 34 wherein in the active agent, $R^1$ is a 3-isoxazolyl.

36. The method of claim 35 wherein in the active agent, $R^3$ is 4-(trifluoromethyl)phenyl.

37. The method of claim 36 wherein the active agent is 1-(2,6-dichlorobenzoyl)-3-(5-(4-trifluoromethyl)phenyl)-3-isoxazolyl)urea.

38. The method of claim 36 wherein the active agent is 1-(2,6-difluorobenzoyl)-3-(5-(4-(trifluoromethyl)phenyl)-3-isoxazolyl)urea.

39. The method of claim 36 wherein the active agent is 1-(2,6-dimethoxybenzoyl)-3-(5-(4-(trifluoromethyl)phenyl)-3-isoxazolyl)urea.

40. The method of claim 36 wherein the active agent is 1-(2-methylbenzoyl)-3-(5-(4-(trifluoromethyl)phenyl)-3-isoxazolyl)urea.

41. The method of claim 36 wherein the active agent is 1-(2-chlorobenzoyl)-3-(5-(4-(trifluoromethyl)phenyl)-3-isoxazolyl)urea.

42. The method of claim 36 wherein the active agent is 1-(2-chloro-6-fluorobenzoyl)-3-(5-(4-(trifluoromethyl)phenyl)-3-isoxazolyl)urea.

43. The method of claim 36 wherein in the active agent, $R^2$ is chloro or bromo.

44. The method of claim 43 wherein the active agent is 1-(2,6-dichlorobenzoyl)-3-(4-chloro-5-(4-trifluoromethyl)phenyl)-3-isoxazolyl)urea.

45. The method of claim 43 wherein the active agent is 1-(2-chlorobenzoyl)-3-(4-chloro-5-(4-(trifluoromethyl)phenyl)-3-isoxazolyl)urea.

46. The method of claim 43 wherein the active agent is 1-(2,6-difluorobenzoyl)-3-(4-chloro-5-(4-(trifluoromethyl)phenyl)-3-isoxazolyl)urea.

47. The method of claim 43 wherein the active agent is 1-(2-chloro-6-fluorobenzoyl)-3-(4-chloro-5-(4-(trifluoromethyl)phenyl)-3-isoxazolyl)urea.

48. The method of claim 43 wherein the active agent is 1-(2-chlorobenzoyl)-3-(4-bromo-5-(4-(trifluoromethyl)phenyl)-3-isoxazolyl)urea.

49. The method of claim 43 wherein the active agent is 1-(2,6-dichlorobenzoyl)-3-(4-bromo-5-(4-(trifluoromethyl)phenyl)-3-isoxazolyl)urea.

50. The method of claim 43 wherein the active agent is 1-(2,6-difluorobenzoyl)-3-(4-bromo-5-(4-(trifluoromethyl)phenyl)-3-isoxazolyl)urea.

51. The method of claim 43 wherein the active agent is 1-(2-chloro-6-fluorobenzoyl)-3-(4-bromo-5-(4-(trifluoromethyl)phenyl)-3-isoxazolyl)urea.

52. The method of claim 35 wherein in the active agent, $R^3$ is 4-(1,1,2,2-tetrafluoroethoxy)phenyl.

53. The method of claim 52 wherein the active agent is 1-(2,6-dichlorobenzoyl)-3-(5-(4-(1,1,2,2-tetrafluoroethoxy)phenyl)-3-isoxazolyl)urea.

54. The method of claim 35 wherein in the active agent, $R^3$ is 3-(trifluoromethyl)phenyl.

55. The method of claim 54 wherein the active agent is 1-(2-chlorobenzoyl)-3-(5-(3-trifluoromethyl)phenyl)-3-isoxazolyl)urea.

56. The method of claim 34 wherein in the active agent, $R^1$ is 5-isoxazolyl.

57. The method of claim 56 wherein in the active agent, $R^5$ is 4-(trifluoromethyl)phenyl.

58. The method of claim 57 wherein the active agent is 1-(2,6-dichlorobenzoyl)-3-(3-(4-(trifluoromethyl)phenyl)-5-isoxazolyl)urea.

59. The method of claim 56 wherein in the active agent, $R^5$ is 3-(trifluoromethyl)phenyl.

60. The method of claim 59 wherein the active agent is 1-(2,6-dichlorobenzoyl)-3-(3-(3-(trifluoromethyl)phenyl)-5-isoxazolyl)urea.

61. The method of claim 56 wherein in the active agent, $R^5$ is trifluoromethyl.

62. The method of claim 61 wherein the active agent is 1-(2,6-dichlorobenzoyl)-3-(3-(trifluoromethyl)-5-isoxazolyl)urea.

63. The method of claim 34 wherein in the active agent, $R^1$ is a 3-benzisoxazolyl.

64. The method of claim 63 wherein the active agent is 1-(2,6-dichlorobenzoyl)-3-(3-benzisoxazolyl)urea.

65. The method of claim 63 wherein in the active agent, $R^6$ is trifluoromethyl.

66. The method of claim 65 wherein the active agent is 1-(2,6-difluorobenzoyl)-3-(6-(trifluoromethyl)-3-benzisoxazolyl)urea.

67. Composition comprising a excipient and an insecticidally effective amount of an active agent which is a compound of claim 1.

68. The composition of claim 67 wherein in the active agent, $R^1$ is 3-isoxazolyl.

69. The composition of claim 68 wherein in the active agent, $R^3$ is 4-(trifluoromethyl)phenyl.

70. The composition of claim 69 wherein the active agent is 1-(2,6-dichlorobenzoyl)-3-(5-(4-trifluoromethyl)phenyl)-3-isoxazolyl)urea.

71. The composition of claim 69 wherein the active agent is 1-(2,6-difluorobenzoyl)-3-(5-(4-trifluoromethyl)phenyl)-3-isoxazolyl)urea.

72. The composition of claim 69 wherein the active agent is 1-(2,6-dimethoxybenzoyl)-3-(5-(4-(trifluoromethyl)phenyl)-3-isoxazolyl)urea.

73. The composition of claim 69 wherein the active agent is 1-(2-methylbenzoyl)-3-(5-(4-(trifluoromethyl)phenyl)-3-isoxazolyl)urea.

74. The composition of claim 69 wherein the active agent is 1-(2-chlorobenzoyl)-3-(5-(4-(trifluoromethyl)phenyl)-3-isoxazolyl)urea.

75. The composition of claim 69 wherein the active agent is 1-(2-chloro-6-fluorobenzoyl)-3-(5-(4-(trifluoromethyl)phenyl)-3-isoxazolyl)urea.

76. The composition of claim 69 wherein in the active agent, $R^2$ is chloro or bromo.

77. The composition of claim 76 wherein the active agent is 1-(2,6-dichlorobenzoyl)-3-(4-chloro-5-(4-(trifluoromethyl)phenyl)-3-isoxazolyl)urea.

78. The composition of claim 76 wherein the active agent is 1-(2-chlorobenzoyl)3-(4-chloro-5-(4-(trifluoromethyl)phenyl)-3-isoxazolyl)urea.

79. The composition of claim 76 wherein the active agent is 1-(2,6-difluorobenzoyl)-3-(4-chloro-5-(4-(trifluoromethyl)phenyl)-3-isoxazolyl)urea.

80. The composition of claim 76 wherein the active agent is 1-(2-chloro-6-fluorobenzoyl)-3-(4-chloro-5-(4-trifluoromethyl)phenyl)-3-isoxazolyl)urea.

81. The composition of claim 76 wherein the active agent is 1-(2-chlorobenzoyl)-3-(4-bromo-5-(4-(trifluoromethyl)phenyl)-3-isoxazolyl)urea.

82. The composition of claim 76 wherein the active agent is 1-(2,6-dichlorobenzoyl)-3-(4-bromo-5-(4-(trifluoromethyl)phenyl-3-isoxazolyl)urea.

83. The composition of claim 76 wherein the active agent is 1-(2,6-difluorobenzoyl)-3-(4-bromo-5-(4-(trifluoromethyl)phenyl)-3-isoxazolyl)urea.

84. The composition of claim 76 wherein the active agent is 1-(2-chloro-6-fluorobenzoyl)-3-(4-bromo-5-(4-(trifluoromethyl)phenyl)-3-isoxazolyl)urea.

85. The composition of claim 68 wherein in the active agent, $R^3$ is 4-(1,1,2,2-tetrafluoroethoxy)phenyl.

86. The composition of claim 85 wherein the active agent is 1-(2,6-dichlorobenzoyl)-3-(5-(4-(1,1,2,2-tetrafluoroethoxy)phenyl)-3-isoxazolyl)urea.

87. The composition of claim 68 wherein in the active agent, $R^3$ is 3-(trifluoromethyl)phenyl.

88. The composition of claim 87 wherein the active agent is 1-(2-chlorobenzoyl)-3-(5-(3-trifluoromethyl)phenyl)-3-isoxazolyl)urea.

89. The composition of claim 67 wherein in the active agent, $R^1$ is 5-isoxazolyl.

90. The composition of claim 89 wherein in the active agent, $R^5$ is 4-(trifluoromethyl)phenyl.

91. The composition of claim 90 wherein the active agent is 1-(2,6-dichlorobenzoyl)-3-(3-(4-(trifluoromethyl)phenyl)-5-isoxazolyl)urea.

92. The composition of claim 89 wherein in the active agent, $R^5$ is 3-(trifluoromethyl)phenyl.

93. The composition of claim 92 wherein the active agent is 1-(2,6-dichlorobenzoyl)-3-(3-(3-(trifluoromethyl)phenyl)-5-isoxazolyl)urea.

94. The composition of claim 89 wherein in the active agent, $R^5$ is trifluoromethyl.

95. The compound of claim 95 wherein the active agent is 1-(2,6-dichlorobenzoyl)-3-(3-trifluoromethyl-5-isoxazolyl)urea.

96. The composition of claim 67 wherein in the active agent, $R^1$ is a 3-benzisoxazolyl.

97. The composition of claim 96 wherein the active agent is 1-(2,6-dichlorobenzoyl)-3-(3-benzisoxazolyl)urea.

98. The composition of claim 96 wherein in the active agent, $R^6$ is trifluoromethyl.

99. The composition of claim 98 wherein the active agent is 1-(2,6-(difluorobenzoyl)-3-(6-(trifluoromethyl)-3-benzisoxazolyl)urea.

* * * * *